(12) United States Patent
Kim et al.

(10) Patent No.: US 10,299,685 B2
(45) Date of Patent: May 28, 2019

(54) METHOD AND APPARATUS TO ENHANCE LIGHT ILLUMINATING INTENSITY AND DIFFUSIVITY

(71) Applicant: University of Pittsburgh—Of the Commonwealth System of Higher Education, Pittsburgh, PA (US)

(72) Inventors: Kang Kim, Pittsburgh, PA (US); Zhaohui Wang, Pittsburgh, PA (US); Seung Han Ha, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 236 days.

(21) Appl. No.: 14/366,666

(22) PCT Filed: Dec. 21, 2012

(86) PCT No.: PCT/US2012/071178
§ 371 (c)(1),
(2) Date: Jun. 18, 2014

(87) PCT Pub. No.: WO2013/096734
PCT Pub. Date: Jun. 27, 2013

(65) Prior Publication Data
US 2015/0005613 A1 Jan. 1, 2015

Related U.S. Application Data

(60) Provisional application No. 61/579,485, filed on Dec. 22, 2011.

(51) Int. Cl.
*A61B 5/00* (2006.01)
*G01N 21/17* (2006.01)
(Continued)

(52) U.S. Cl.
CPC .......... *A61B 5/0095* (2013.01); *A61B 5/441* (2013.01); *A61B 5/4836* (2013.01);
(Continued)

(58) Field of Classification Search
CPC ..... A61B 5/0095; A61B 5/441; A61B 5/4836; A61N 2005/063; A61N 5/0616;
(Continued)

(56) References Cited

U.S. PATENT DOCUMENTS 4,503,564 A * 3/1985 Edelman .............. H04R 23/008
381/164
4,657,397 A * 4/1987 Oehler ...................... G01J 1/04
250/343

(Continued)

FOREIGN PATENT DOCUMENTS

JP 2004-201749 7/2004

OTHER PUBLICATIONS

International Search Report and Written Opinion from International Application No. PCT/US2012/071178, dated Apr. 29, 2013, 8 pages.

*Primary Examiner* — Katherine Fernandez
(74) *Attorney, Agent, or Firm* — Klarquist Sparkman, LLP

(57) ABSTRACT

Photoacoustic probes include reflective surfaces situated to redirect scattered or reflected optical radiation from a specimen surface back to the specimen. A reflective coating can reflect probe radiation while transmitting visible radiation so that a technician can view the specimen. One or more optical fibers and acoustic transducers can be secured to a lens or other substrate on which the reflective surface is defined. The light collector is configured to block scattered light so that an operator and a subject are not exposed to the scattered light.

25 Claims, 7 Drawing Sheets

(51) Int. Cl.
  *G01N 21/47* (2006.01)
  *G01N 29/06* (2006.01)
  *G01N 29/24* (2006.01)
  *A61N 5/06* (2006.01)

(52) U.S. Cl.
  CPC ....... *A61N 5/0616* (2013.01); *G01N 21/1702* (2013.01); *G01N 21/474* (2013.01); *G01N 29/0654* (2013.01); *G01N 29/2418* (2013.01); *A61N 2005/063* (2013.01)

(58) Field of Classification Search
  CPC ............. G01N 21/1702; G01N 21/474; G01N 29/0654; G01N 29/2418
  See application file for complete search history.

(56) References Cited

U.S. PATENT DOCUMENTS

| | | | | |
|---|---|---|---|---|
| 4,981,343 | A * | 1/1991 | Folsom | G02B 6/4206 359/726 |
| 5,521,657 | A | 5/1996 | Klopotek et al. | |
| 6,216,540 | B1 | 4/2001 | Nelson et al. | |
| 6,236,455 | B1 * | 5/2001 | Autrey | G01N 21/1702 356/246 |
| 2002/0102749 | A1 | 8/2002 | Fielden et al. | |
| 2003/0199857 | A1 * | 10/2003 | Eizenhofer | A61B 17/22004 606/2.5 |
| 2004/0218145 | A1 * | 11/2004 | Matsumoto | A61B 3/1025 351/214 |
| 2006/0184042 | A1 * | 8/2006 | Wang | A61B 5/0073 600/476 |
| 2008/0071172 | A1 | 3/2008 | Bruck et al. | |
| 2008/0188724 | A1 * | 8/2008 | Hwang | A61B 5/0095 600/316 |
| 2011/0275890 | A1 * | 11/2011 | Wang | A61B 5/0062 600/104 |
| 2011/0282181 | A1 * | 11/2011 | Wang | A61B 5/0095 600/407 |
| 2012/0204648 | A1 * | 8/2012 | Wang | A61B 5/0095 73/606 |

\* cited by examiner

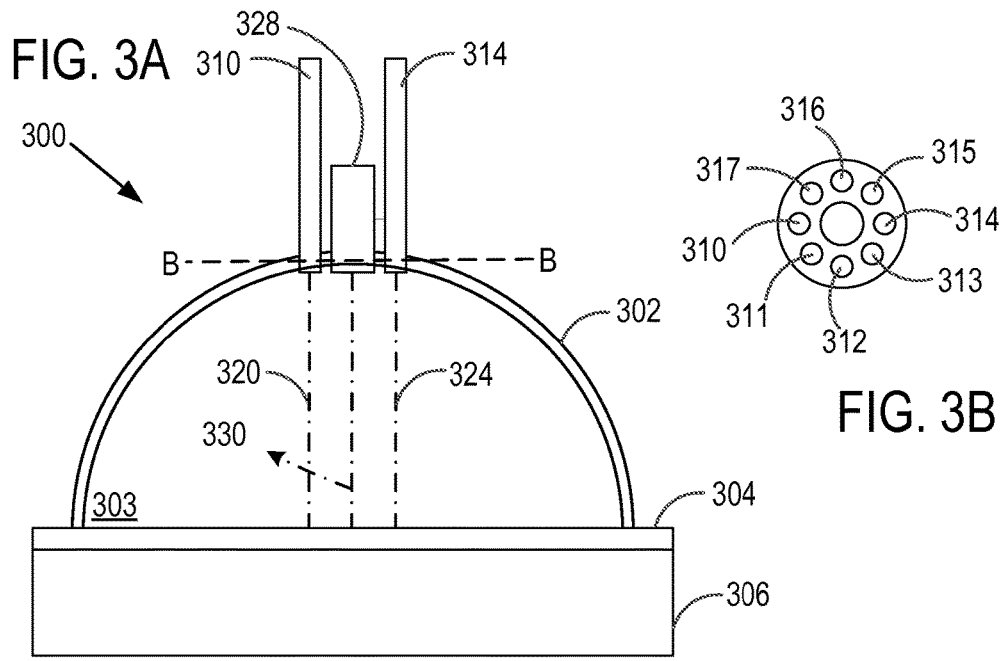
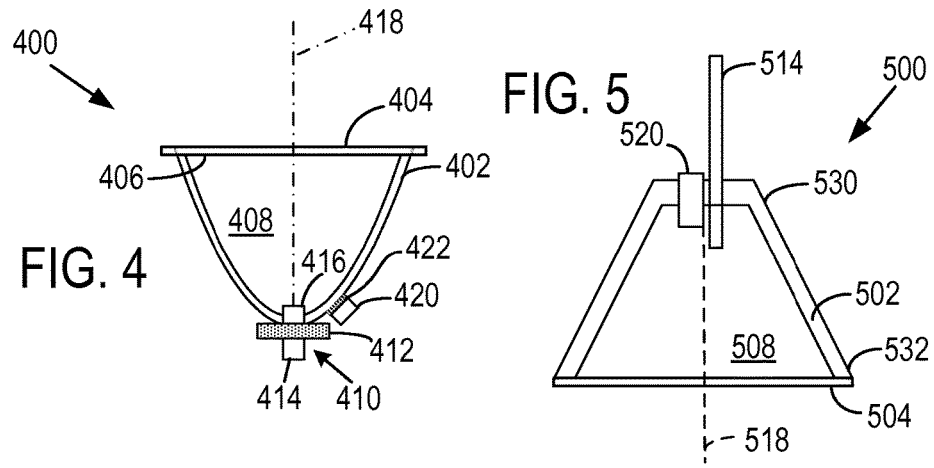
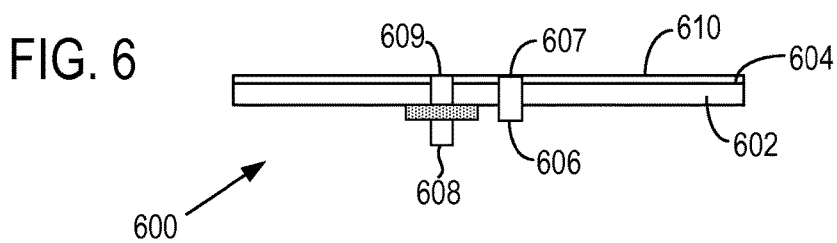

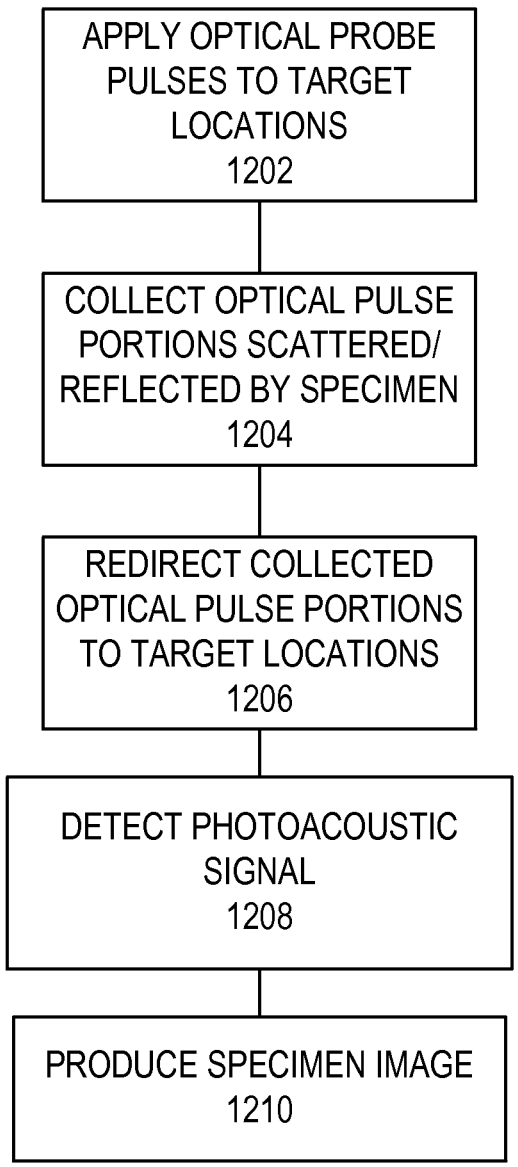

METHOD AND APPARATUS TO ENHANCE LIGHT ILLUMINATING INTENSITY AND DIFFUSIVITY

CROSS REFERENCE TO RELATED APPLICATIONS

This is the U.S. National Stage of International Application No. PCT/US2012/071178, filed Dec. 21, 2012, which was published in English under PCT Article 21(2), which in turn claims the benefit of U.S. Provisional Application No. 61/579,485, filed Dec. 22, 2011. The provisional application is incorporated herein by reference in its entirety.

FIELD

The disclosure relates to photoacoustic probes and imaging methods.

BACKGROUND

Photoacoustic imaging (PAI) is an emerging biomedical imaging modality based on the photoacoustic effect. In PAI, light pulses (often from a laser) are delivered to a target locus ("situs") in or on a sample. Some of the pulse energy is absorbed at the situs and converted into heat. The transient heating causes a corresponding transient thermoelastic expansion of the situs, which produces a corresponding wideband ultrasonic emission from the situs. The generated ultrasonic waves are detected using one or more ultrasonic transducers that convert the detected waves into corresponding electrical pulses that are processed into corresponding images.

The optical absorption of light by a biological sample is closely associated with certain physiological properties such as hemoglobin concentration and/or oxygen saturation. As a result, the magnitude of ultrasonic emission (i.e., the photoacoustic signal, proportional to the local energy deposition) from the situs reveals physiologically specific optical absorption contrast that facilitates formation of 2-D or 3-D images of the situs. Blood usually exhibits greater absorption than surrounding tissues, providing sufficient endogenous contrast to allow PAI of blood vessels and tissues. For example, PAI can produce high-contrast images of breast tumors in situ due to the greater optical absorption by the increased blood supply provided to the tumor. While conventional X-ray mammography and ultrasonography produce images of benign features as well as pathological features, PAI can produce information more specific to the malignant condition, such as enhanced angiogenesis at a tumor site.

Another important imaging modality for various disease-related and other purposes is ultrasonic scanning, which has high sensitivity but low tissue specificity. Ultrasonic imaging is performed using an ultrasonic scanning machine to which a "probe" comprising one or more piezoelectric transducers is connected. Electrical pulses produced by the machine are converted by certain of the piezoelectric transducer(s) into corresponding ultrasound pulses of a desired frequency (usually between 1 and 70 MHz). The ultrasound is focused either by the shape of the sending transducer(s), a "lens" in front of the transducer, or a complex set of control pulses from the ultrasonic scanning machine. Focusing produces a shaped acoustic wave propagating from the transducer. The sound wave enters the sample (e.g., a subject's body) and converges to focus at a desired depth in the sample. Most ultrasonic probes include a face member made of a material providing impedance matching for transmitting ultrasonic pulses efficiently into the subject's body. A hydrogel is usually applied between the subject's skin and the face member of the probe for efficient propagation of sound waves to and from the probe. Portions of the sound wave are reflected from various tissue layers and structures in the sample, particularly from loci exhibiting density changes. Some of the reflected sound returns to the probe, in which certain transducer(s) convert the received sound into corresponding electrical pulses that are converted by the ultrasonic scanning machine into an image.

One of the challenges in photoacoustic (PA) imaging for in vivo animal study and eventual clinical translation is the limited penetration depth of the source light. Near infrared light allows PA imaging up to a few centimeters deep in soft tissues, but typically with unacceptable signal-to-noise ratio. Some applications require large depths that are limited by attenuation of source laser light propagating through soft tissues. A large portion of light energy directed into soft tissues is reflected and lost at the skin surfaces. In addition, irradiation with non-uniform optical beams can produce measurement artifacts that are more closely related to optical beam non-uniformity rather than specimen features. A non-uniformly diffused laser beam to the skin with high power may also cause damage such as burning.

SUMMARY

Disclosed herein are methods and apparatus that can enhance the effective intensity and diffusivity of a light source used to illuminate a specimen, especially specimens that exhibit substantial scattering. In one embodiment, apparatus consists of a conical or spherical light collector (or collimator) having a highly reflective coating on an interior surface and a single element light source or light source array embedded to the inner side of the collector. A highly reflective surface inside a collector captures reflected and scattered light from a target surface, increasing an effective irradiation intensity. In addition, collector can provide multiple bouncing of light in random directions and a more uniform redistribution of light energy onto a target surface. An increased intensity can permit imaging deeper into tissues or optically based treatment of deeper tissues. In one example, such light collectors are used in photoacoustic imaging. The disclosed apparatus and methods reduce light loss due to, for example, skin surfaces that are typically highly reflective and scattering. The disclosed apparatus and methods also tend to provide uniform irradiation, even from laser sources with non-uniform beams.

Photoacoustic probes for delivering optical pulses to a target and receiving associated acoustic signals comprise a light collector situated along an axis, the light collector defining a reflective surface and including an optical input aperture configured to couple optical pulses to a target through a volume defined by the reflective surface and a reflector output aperture, and to direct portions of the optical beam received from the target back to the target. An acoustic aperture is configured to receive acoustic signals associated with the optical beam and couple the received acoustic signals to an acoustic transducer. In some examples, the optical input aperture or the acoustic aperture is situated along the axis. In some embodiments, the reflective surface is a concave surface or a planar surface. In other embodiments, the reflective surface is situated at an inner or an outer surface of a concave shell, or at a convex surface of a plano-convex lens or a plano surface of a plano-plano lens. In representative examples, the reflective surface is configured to reflect an infrared optical beam and transmit visible optical radiation. In typical examples, at least one acoustic transducer is secured to the lens and configured to receive the acoustic signals associated with the optical beam and an optical fiber is situated so as to direct optical pulses through the optical input aperture to the target. In some examples, at least one of the input aperture and acoustic aperture are defined by corresponding holes in the reflective surface or the input aperture is defined by a light transmissive window in the reflective surface. In typical examples, an acoustic transducer is fixed with respect to the reflective surface and situated to receive the acoustic signal, and an optical fiber is fixed with respect to the reflective surface and configured to deliver the optical beam to the target through the output aperture. In other alternatives, the light collector comprises a transmissive face layer situated at the reflector output aperture, and configured to retain an acoustic index matching material so as to acoustically couple the acoustic aperture and the face layer. In some embodiments, the light collector includes a concave shell, and the reflective surface is defined on at least one surface of the concave shell. In typical examples, an acoustic transducer is secured to the concave shell and situated to receive the acoustic signal, and an optical fiber is secured to the concave shell and configured to deliver the optical beam to the target through the output aperture.

Methods comprise directing an optical beam to a target and capturing at least a portion of the optical beam returned from the target. A captured beam is directed to the target based on the captured portion of the optical beam. In some examples, at least one acoustic signal produced at the target responsive to the optical beam and the captured beam is detected. In representative embodiments, the portion of the optical beam returned from the target is captured with a concave reflective surface, and the optical beam is directed to the target from an aperture in the concave reflective surface. In other embodiments, a plurality of acoustic signals returned from the target are processed so as to from a target image.

Photoacoustic imaging systems comprise an optical pulse source configured to direct optical pulses to a target. An acoustic transducer is configured to detect acoustic signals produced in response to the optical pulses directed to the target and a signal processor is configured to receive the detected acoustic signals and produce an image based on the detected acoustic signals. A light collector is situated to receive portions of the optical probe returned from the target, and direct the collected portions back to the target. In some embodiments, the light collector includes a surface configured to reflect the received portions of the optical probe returned from the target back to the target. In representative examples, the reflective surface is a planar surface or a concave surface. In typical systems, the optical pulses are at a wavelength near infrared wavelengths, but infrared and visible wavelengths can be used as well. If infrared or near infrared wavelengths are used, the reflective surface can be configured to transmit visible optical radiation so that the target is viewable through the light collector. In some examples, the light collector comprises a plano-convex lens, and the reflective surface is defined on the convex surface of the plano-convex lens, and the acoustic transducer is secured to the plano-convex lens. In still other examples, the concave surface of the light collector includes a target-side aperture, and comprises a transmissive layer situated at the target-side aperture so as to define a reflector volume. The transmissive layer is configured to retain an acoustic index matching material and transmit the optical pulses and the acoustic signals.

The foregoing and other objects, features, and advantages of the disclosed technology will become more apparent from the following detailed description, which proceeds with reference to the accompanying drawings.

BRIEF DESCRIPTION OF THE DRAWINGS

FIGS. 3A-3B are schematic diagrams of a representative PA probe with a plurality of optical fiber inputs.

FIG. 4 is a schematic diagram of a representative PA probe having a parabolic reflector.

FIG. 5 is a schematic diagram of a representative PA probe having a truncated conic reflector.

FIG. 6 is a schematic diagram of a representative PA probe having a planar reflector.

FIG. 12 is a block diagram of a representative PA measurement method.

DETAILED DESCRIPTION

Figure 1:
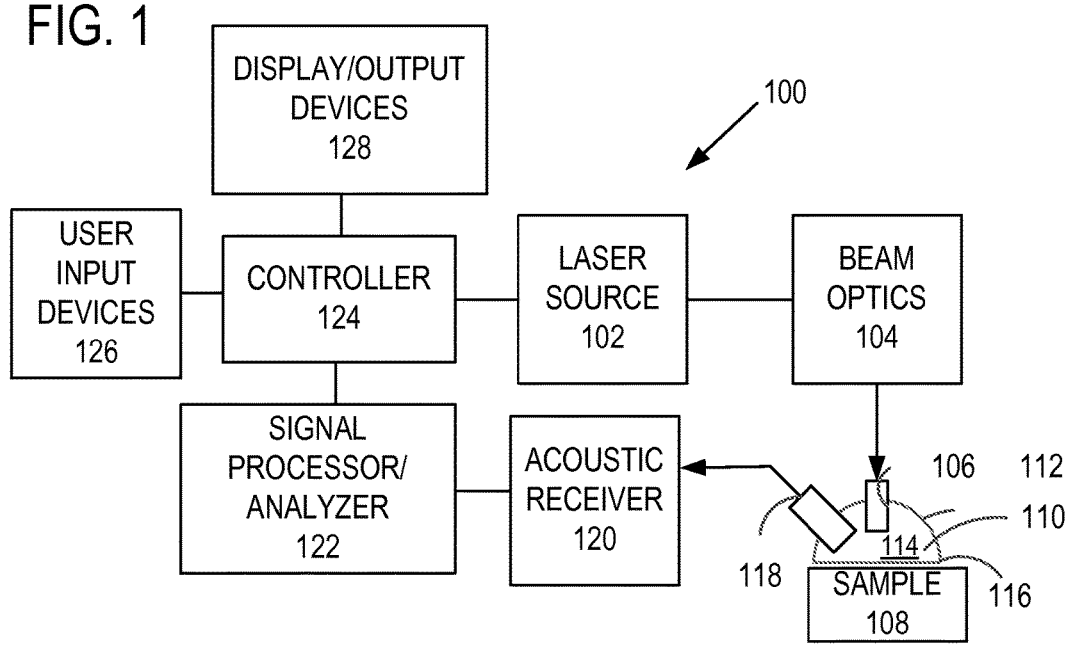
FIG. 1 is a schematic diagram of a representative photoacoustic (PA) measurement system configured to redirect probe pulse radiation scattered or reflected by a sample back to the sample.

The following disclosure is presented in the context of representative embodiments that are not to be construed as being limiting in any way. This disclosure is directed toward all novel and non-obvious features and aspects of the various disclosed embodiments, alone and in various combinations and sub-combinations with one another. The disclosed methods, apparatus, and systems are not limited to any specific aspect or feature or combination thereof, nor do the disclosed embodiments require that any one or more specific advantages be present or problems be solved.

Although the operations of the disclosed methods are described in a particular, sequential order for convenient presentation, it should be understood that this manner of description encompasses rearrangement of the operations, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other things and methods.

This disclosure sometimes uses terms like "produce," "generate," "select," "receive," "exhibit," and "provide" to describe the disclosed methods. These terms are high-level abstractions of the actual operations that are performed. The actual operations that correspond to these terms may vary depending on the particular implementation and are readily discernible by one of ordinary skill in the art.

The singular forms "a," "an," and "the" include the plural forms unless the context clearly dictates otherwise. The term "includes" means "comprises." Unless the context dictates otherwise, the term "coupled" means mechanically, electrically, or electromagnetically connected or linked and includes both direct connections or direct links and indirect connections or indirect links through one or more intermediate elements not affecting the intended operation of the described system.

Certain terms may be used such as "up," "down," "upper," "lower," and the like. These terms are used, where applicable, to provide some clarity of description when dealing with relative relationships. But, these terms are not intended to imply absolute relationships, positions, and/or orientations.

The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, percentages, temperatures, times, and so forth, as used in the specification or claims are to be understood as being modified by the term "about" or "approximately." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

The following explanations of terms are provided to better describe the present disclosure and to guide those of ordinary skill in the art in the practice of the present disclosure.

Photoacoustic imaging (PAI) is an imaging technique exploiting the photoacoustic effect. In typical PAI methods, light pulses produced by a laser are focused at a small region in a sample. The resulting intermittent heating of the exposed region causes material in the region to expand and contract. The resulting oscillatory motion of the exposed region generates acoustic waves that propagate through the sample and can be detected and interpreted to form an image using conventional ultrasonic imaging methods and apparatus. In PAI, images are typically associated with local optical absorption in the sample. Three-dimensional imaging is possible. While optical absorption in a sample can be used to produce acoustic signals for PAI, other light/specimen interactions can produce acoustic signals as well, and some such interactions are described below. The disclosed methods and apparatus are not limited to any particular method of generating acoustic signals in response to continuous wave or pulsed optical beams. The disclosed light collectors can also be used to deliver therapeutic laser light for photothermal or photodynamic therapy. In some cases, PAI and phototherapy can be performed with a common light collector so that regions of interest can be identified before phototherapeutic exposure. Different exposure sources at different or the same wavelengths can be used, an applied using the same light collector as used in PAI.

Thermal Expansion

Ion specific absorption in a laser illuminated region produces heat due to non-radiative relaxation, causing expansion in the region. If a laser pulse duration is short, the resulting thermal expansion will be correspondingly fast. This laser induced thermal expansion causes the illuminated region to extend and compress, and, as a result, an acoustic wave is generated.

Vaporization and Boiling

If the absorbed laser energy density within an absorbing region exceeds a certain threshold (for water, for example, the threshold is about 2.24 kJ/cm$^3$) determined by the optical and thermal properties of the medium, the generated heat may cause vaporization and internal boiling. In this case, the conversion efficiency of optical pulse energy to acoustic emission is much higher that associated with thermal expansion.

Optical Breakdown

Optical breakdown is caused by the interaction of a medium and an optical beam with a very high optical intensity. In a pure medium, the threshold can be as high as $10^{10}$ W/cm$^2$. Optical breakdown may generate a strong acoustic wave, and this mechanism may be an efficient process for converting optical energy into acoustic energy. Optical breakdown can be realized even in transparent media, in which acoustic generation caused by ordinary absorption does not occur.

Photochemical Processes

Photochemical effects such as gas evolution and consumption, and photochemical chain reactions are also capable of generating acoustic emissions. Gas evolution or consumption may produce a larger photoacoustic signal than that associated with thermal expansion. A photochemical chain reaction may cause a large and prolonged photoacoustic emission.

Contrast Agents

Contrast agents can be used in both PAI and phototherapy and include PA contrast agents, endogeneous or exogeneous materials, dyes, polymers, combinations of chemicals, metal-based synthetic materials, non-metal based synthetic materials, or any other materials for contrast-enhanced imaging, drug delivery, or photothermal or photodynamic therapy.

As used herein, ultrasound refers to acoustic signals having frequencies between 10 kHz and 20 GHz. Optical beams, optical radiation, and light refer to propagating electromagnetic radiation at wavelengths between about 200 nm and 3000 nm. The term "optical beam" is used for convenient description and does not imply any particular beam collimation, and as used herein, optical beams can be associated with numerical apertures as large as 1. Optical surfaces are referred to as concave or convex. Light collectors can include concave optical surfaces. A concave optical surface as used herein is an optical surface having a center of curvature (or an effective or approximate center of curvature for non-spherical surfaces) that is situated on a target side of a light collector reflective surface. In addition, in some examples, plano-convex lenses are used, but in these examples, the "convex" lens surface is situated so as to be a concave surface as defined above, and the term plano-convex is used to conform to customary usage with respect to such lenses. Images and imaging systems are disclosed, and as used herein, an image refers to a data set in any form (such as TIFF, JPEG, or other format) and that can be stored in a computer readable device such as RAM, ROM, a hard disk. A displayed image is an image provided on a display device for viewing by a user.

The disclosed light collectors are described in the examples with reference to PAI, but can also be used to provide more diffuse irradiation of specimen surfaces, and thus can reduce the specimen damage such as tissue burning, and/or permit photo-exposure at higher fluences in photo-therapeutic exposures, with or without any associated PAI of the specimen.

Referring to FIG. 1, a representative photoacoustic (PA) imaging system 100 includes a pulsed laser source 102 that is coupled to beam optics 104 configured to produce optical probe pulses focused to a selected size and/or shape that are then directed to an optical fiber section 106. The optical fiber section 106 is situated to direct the optical probe pulses to a sample 108. A light collector 110 is situated to receive portions of the optical probe pulses reflected, refracted, scattered, or otherwise returned from the sample 108. The light collector 110 includes a reflective surface 112 that can be provided as a metallic or dielectric coating on a hemispherical, parabolic, elliptical, ovoid, polygonal, or other concave surface, including other aspheric shapes and shapes defined by multiple segments having different shapes and orientations. Some such surfaces correspond to surfaces of concave optical elements that are rotationally symmetric about an axis. Examples of such surfaces include paraboloids, ellipsoids, and spheroids. However, surfaces need not be rotationally symmetric. In addition, a plurality of segmented reflective surfaces can also be used to form a reflective concave surface. In some examples, hollow reflective shells such as metallic reflectors are used. In other examples, solid refractive optical elements can be used to which a suitable reflective coating has been applied.

As shown in FIG. 1, the optical fiber section 106 extends into a volume 114 defined by the reflective surface 112 and an exit aperture 116. If the volume 114 is defined by a reflective shell, the volume 114 can be filled with water or other material so as to provide acoustic matching to the sample 108. If the volume 114 corresponds to a solid optical element, an acoustic matching material can be applied between the exit aperture 116 and the sample 108, but is not shown in FIG. 1.

An acoustic transducer 118 extends into the volume 114 and is situated so as to receive acoustic signals from the sample in response to optical pulses produced by the pulsed laser source 102. In other examples, positions of the acoustic transducer 118 and the optical fiber 106 are exchanged. The acoustic transducer 118 is coupled to an acoustic receiver 120, and detected acoustic signals are coupled to a signal processor/analyzer 122 that processes the detected acoustic signals so as to produce an image of a portion of the sample 108, or other characterization of the sample 108. A controller 124 is coupled to one or more user input devices 126 and one or more display or other output devices 128. The controller 124 is configured to control sample scan rates, adjust laser pulse intensities and durations, select acoustic receiver detection characteristics, and store image data or other data in one or more memory devices such as RAM, a hard disk, or to communicate data to a local area network LAN or a wide area network WAN such as the internet. The controller 124, user input devices 126, and display devices 128 are shown as directly connected to the acoustic receiver 120 and the laser source 102, but a networked computing device that is remote or local can be used as well.

Figures 2A, 2B:
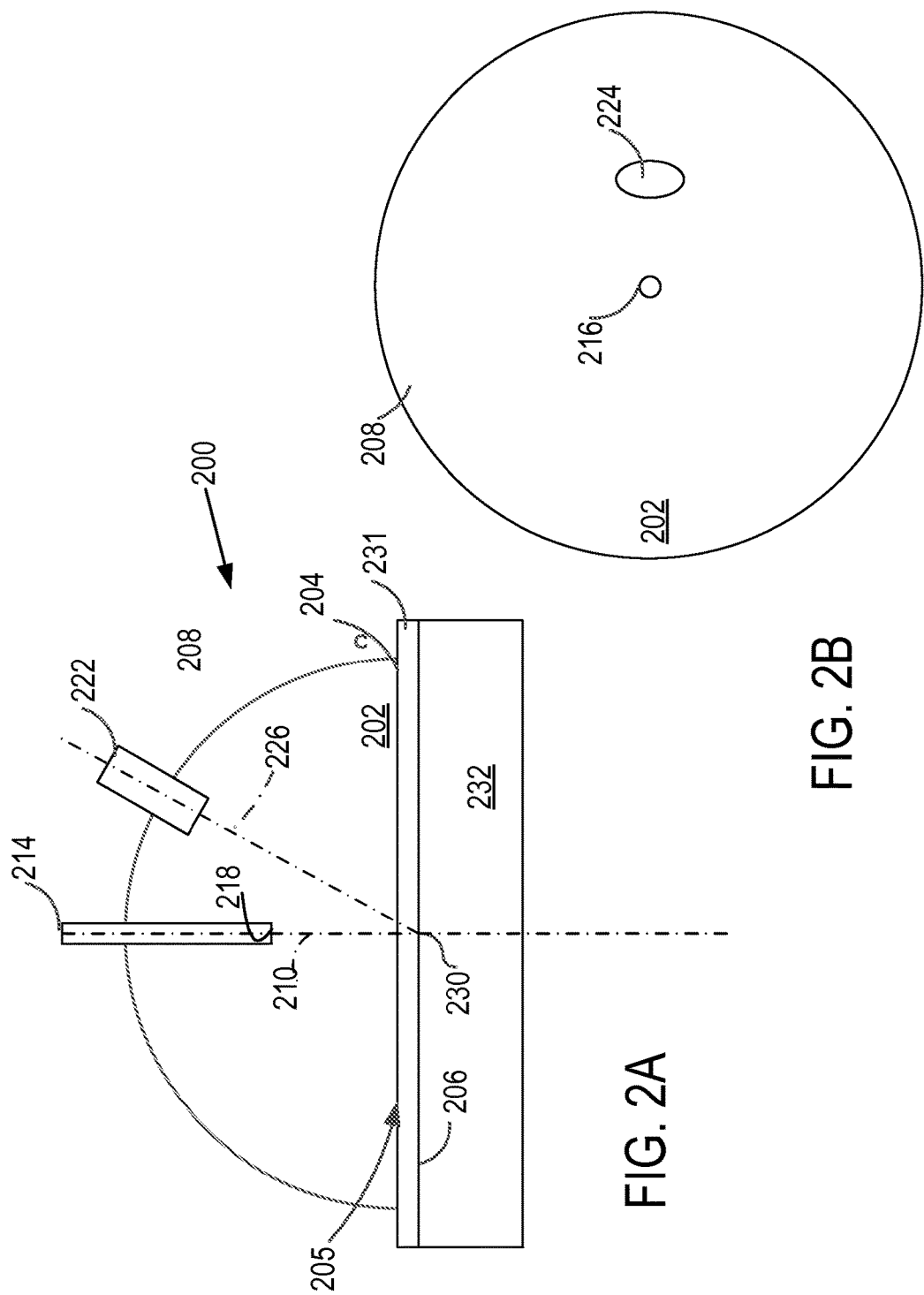
FIGS. 2A-2B are schematic diagrams of a representative PA probe.

FIGS. 2A-2B illustrate a representative photoacoustic probe 200 configured for photoacoustic specimen evaluation. The probe 200 includes a plano-convex lens 202 situated so that a plano surface 204 is proximate a target surface 206. A convex surface 208 is situated along an optical axis 210 and is arranged so as that a center of curvature is on a specimen side of the convex surface 208. The convex surface 208 is provided with a dielectric or other reflective coating. In this arrangement, a light flux from the surface 204 and within a contact area 205 of the plano surface 204 is reflected by the convex surface 208 back to the contact area 205 of the surface 204. For convenience, the convex surface 208 can be referred as a concave surface with respect to the target surface 204.

An optical fiber 214 is inserted into a cavity 216 in the lens 202 and is situated so that an optical beam emitted from an end surface 218 is directed along the optical axis 210. In other examples, the cavity 216 can be situated so as to be displaced from the optical axis 210 so that an optical beam is emitted toward the specimen surface 204 in a direction that is either parallel to or not parallel to the optical axis 210.

An acoustic transducer 222 is inserted into a cavity 224 in the lens 202 so as to receive acoustic signals generated in response to the optical beam from the optical fiber 214. The acoustic transducer 222 is situated along an acoustic axis 226 that intersects the optical axis 210 at an intersection 230. In some examples, the intersection 230 is situated within a target 232, or within the lens 202. The axes 210, 230 need not intersect, and in some cases, are parallel. As shown in FIG. 2B, the plano surface 204 is acoustically coupled to the target 232 with a layer 231 of an acoustic gel, water, or other acoustic matching material.

A plan view of the lens 202 is shown in FIG. 2B. The cavity 216 is typically configured to retain the optical fiber 202, but can be configured to retain focusing optical elements such as one or more lenses. In addition, the surface 208 of the lens 202 can be provided with a curved or planar window region to receive an optical beam. Alternatively, a bottom surface of the cavity 216 can be curved or planar for shaping and entry of an optical beam. The acoustic transducer 222 can be placed in acoustic contact with the surface 208 of the lens 202, and the acoustic transducer cavity 224 is not needed.

Referring to FIGS. 3A-3B, a photoacoustic probe 300 includes a reflector 302 that is situated at a surface layer 304 of a substrate 306. In typical examples, the surface layer 304 is skin, and the substrate 306 is tissue. As shown in FIG. 3B, optical fibers 310-317 are situated so as deliver respective optical beams to the surface layer 304 and extend into an interior 303 of the reflector 302. The optical fibers 310-317 are arranged so as to be equally angularly spaced and equidistant about a reflector axis 330, but more or fewer fibers can be used, and the fibers need not be equally spaced or equidistant as shown. FIG. 3A shows the fibers 310, 314 and associated optical axes 320, 324 that are parallel to the reflector axis 330. The optical fibers 310-317 can be arranged to have axes in a variety of directions, and the configuration of FIGS. 3A-3B is only a convenient example. An acoustic transducer 328 is situated along the axis 330 of the reflector 302 to receive acoustic signals generated in response to optical pulses applied via the optical fibers 310-317.

The reflector 302 is selected to reflect at wavelengths associated with input optical pulses used to generate acoustic signals with a suitable conductive or dielectric coating. For tissue measurement and imaging, optical wavelengths of between about 700 nm and 1700 nm are convenient due to the associated penetration depths in tissue as well as the availability of optical pulse sources. Wavelengths between about 750 nm to 850 nm can be used, and the reflective coating configured to reflect optical radiation at these wavelengths. In other examples, wavelengths between about 200 nm and 3000 nm are used. Reflectivities can be 50%, 75%, 90%, 95%, 99% or higher at optical pulse wavelengths so as to produce increased PA signal magnitudes. In addition, a reflective coating can prevent high power laser pulse radiation from escaping the reflector 302, or attenuate escaping optical power to be at or near safe levels. In some examples, the reflective coating also permits transmission of visible light through the reflector so that a technician using the PA probe 300 can view the target surface 304. For example, if 780 nm laser pulses are used to stimulate a PA signal, shortwave pass dielectric filters having a reflectivity of 80%, 90%, 95%, or 99% at 780 nm can be used. For additional safety, the reflector 302 can be formed of a filter glass or other absorbing material selected to absorb optical pulse radiation. Representative filter glasses include SCHOTT optical filter glasses such as BG38, BG18, BG39, BG40, or heat absorbing glasses such as KG5, depending on optical pulse wavelength.

With reference to FIG. 4, a photoacoustic probe 400 includes a parabolic reflector 402 and a transparent layer 404 secured at an aperture 406 of the parabolic reflector 402. In internal volume 408 of the parabolic reflector 402 is filled with an acoustic coupling material such as an acoustic coupling gel or water. An optical fiber connector 410 includes a mounting flange 412 and a fiber section 414 that extends into the internal volume 408. The fiber section 414 is situated so that an exit surface 416 directs optical pulses along an axis 418 of the parabolic reflector 402. The exit surface 416 can be situated at a focus of the parabolic surface 502 or at another location. In other examples, the fiber section 414 can be differently oriented. An acoustic transducer 420 is acoustically coupled to the parabolic reflector 402 with a layer 422 of an acoustic gel. Alternatively, an acoustic transducer can be situated within the volume 408, and electrical connections to an acoustic transducer can be made via one or more holes in the parabolic reflector 402. The parabolic reflector 402 is provided with a dielectric or other coating so as to reflect at a wavelength associated with the PA optical pulses and transmit sufficient visible light so that a target surface remains viewable.

FIG. 5 illustrates a photoacoustic probe 500 that includes reflector 502 formed as a truncated cone. The reflector 502 is terminated at a specimen end with a transparent layer 504 so as to define an internal volume 508 that can be filled with an acoustic matching material. The reflector 502 tapers along an axis 518 from a first end 530 to a second, typically wider end 532. An acoustic transducer 520 and an optical fiber 514 extend into the volume 508, and are oriented along axes parallel to the axis 518. In some examples, the acoustic transducer 520 and the optical fiber 514 are oriented along other axes, and in cases, along axes that intersect in or outside of the volume 508. The reflector 502 is typically formed of a transparent material that permits specimen viewing through the reflector walls. A coating is generally provided that reflects optical pulse radiation while still permitting viewing.

In another example shown in FIG. 6, a PA probe 600 includes a planar substrate 602 to which a suitable reflective coating layer 604 is applied. An acoustic transducer 606 and an optical fiber 608 are secured in respective apertures for exposure of a specimen to probe pulses and detection of PA pulses. To simply placement of the PA probe 600, end surfaces 609, 607 of the optical fiber 608 and the acoustic transducer 606, respectively, are coplanar with a probe exit surface 610. In use, an acoustic gel is applied at the exit surface 610 to provide acoustic coupling between the probe 600 and a specimen.

Figure 7:
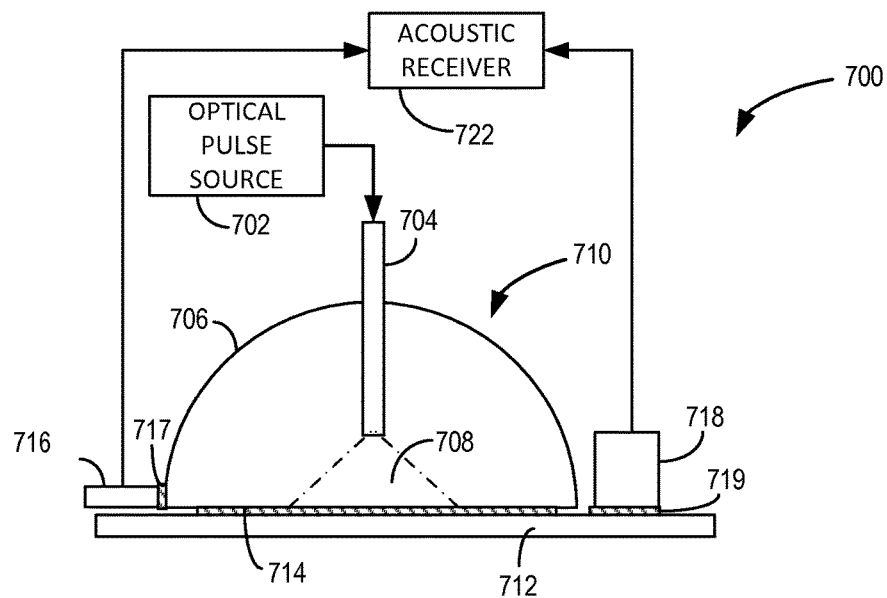
FIG. 7 is a block diagram of a representative PA imaging system that includes an acoustic transducer coupled to a specimen surface.

FIG. 7 is a schematic view of a representative PA system 700. An optical pulse source 702 is situated to provide a pulsed optical beam to an optical fiber 704 that extends through a reflective surface 706. The reflective surface 706 can be provided as a convex surface of a plano-convex lens element 710 or with a concave reflector. A pulsed optical beam input to the optical fiber 704 produces a cone of radiation 708 that is directed to a specimen of interest 712 through an acoustic coupling layer 714. Acoustic transducer 716 is acoustically coupled to the reflective surface 706 (the convex surface of the lens element 710) with an acoustic coupling layer 717. Acoustic transducer 719 is acoustically coupled to the specimen 712 with an acoustic coupling layer 719. The acoustic transducers 716, 718 are electrically coupled to an acoustic receiver 722 that processes transducer electrical signals by buffering, amplification, filtering, or other processes. The processed signals are used by an image processing system (not shown) to provide one or more PA images of the specimen 712.

Figure 8:
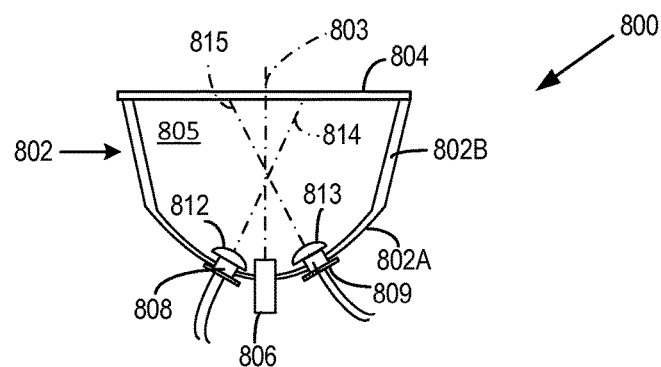
FIG. 8 is a schematic diagram of a representative PA probe having a segmented reflector configured to retain laser diodes or other optical radiation sources.

FIG. 8 illustrates a PA probe 800 that includes a segmented reflector having a spherical portion 802A and a conical portion 802B situated along an axis 803. The segmented reflector 802 is terminated at an output or specimen side with a transparent layer 804. A volume 805 of the reflector 802 is filled with an acoustically transmissive material such as water or an acoustic gel. An acoustic transducer 806 extends into the volume 805 and is situated along the axis 803 of the reflector 802. Laser diodes 808, 809 are situated to extend into the volume 805 and are optically coupled to lenses 812, 813, respectively, so as to direct pulsed optical beams toward the transparent layer 804 along respective axes 814, 815. In the example of FIG. 8, the axes 803, 814, 815 are configured to intersect within the volume 805 but other arrangements can be used. Two laser diodes are illustrated in FIG. 8, but one or more can be provided.

Figure 9:
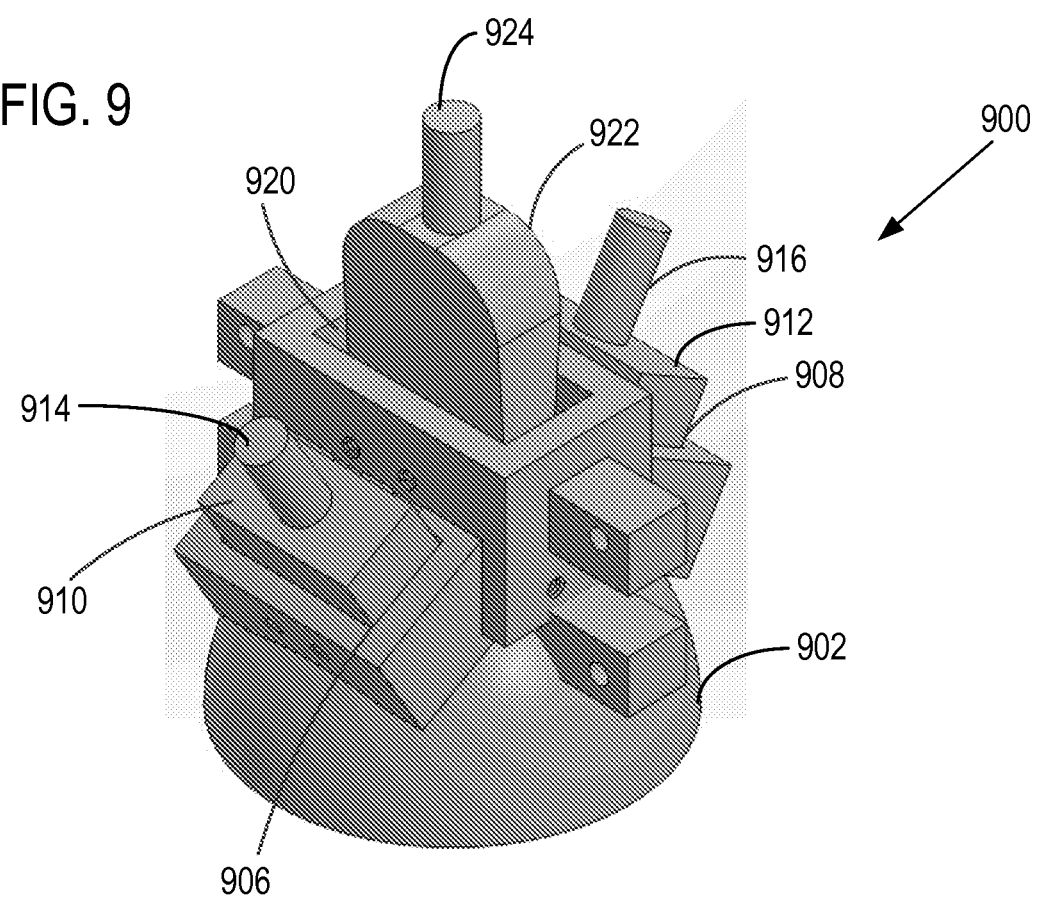
FIG. 9 is a perspective view of a PA probe that includes optical fiber arrays and an acoustic transducer array.

FIG. 9 is perspective view of representative PA probe 900 that includes a reflector 902 formed as a portion of spherical shell or shell of some other shape. As discussed above, the reflector 902 is configured to capture pulsed optical radiation scattered or reflected by a specimen and return the captured radiation to the specimen while permitting a technician to view the specimen through the reflector 902. Fiber array housings 906, 908 fixed to the reflector 902 are arranged to receive respective fiber arrays 910, 912 that receive pulsed optical radiation from respective fiber bundles 914, 916. An acoustic array housing 920 is fixed to the reflector 902 and is configured to receive an acoustic transducer array 922 that communicates acoustic transducer electrical signals via an electrical cable 924. The housings 906, 908, 920 can be formed integrally with the reflector 902, or provided separately and secured to the reflector. Fewer or more optical fiber arrays can be provided, and can be situated on the reflector 902 at other locations. Optical fiber and acoustic transducer locations can be interchanged, and one or more housings can be configured to receive both an acoustic transducer array and an optical fiber array. The fiber arrays 910, 912 can be configured to provide optical beams at one or more wavelengths. For example, a first wavelength can be selected for pulses that generate PA signals and a second wavelength used for therapeutic exposures.

Figure 10A:
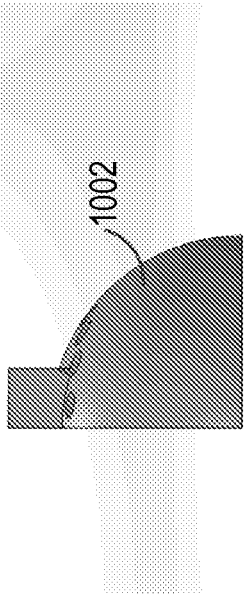
FIGS. 10A-10D are views of a segment of a PA probe.
Figure 10B:
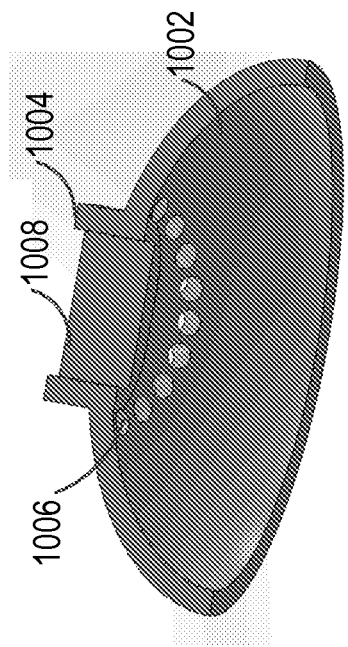
Figure 10C:
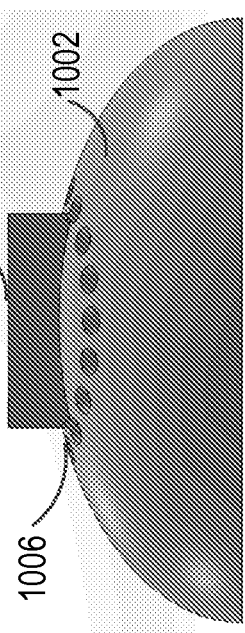
Figure 10D:
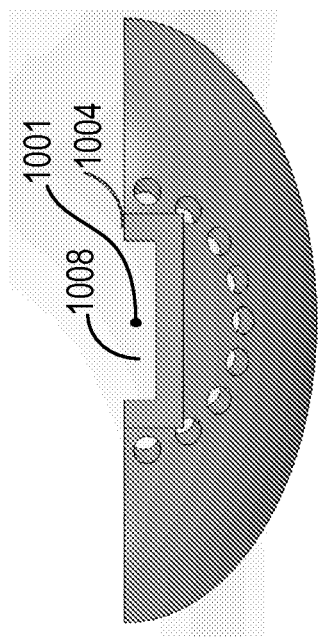

FIGS. 10A-10D illustrate construction of a representative reflector suitable for use in a PA probe. The reflector is formed with first and second reflector segments such as segment 1002. In the example of FIGS. 10A-10B, two substantially similar segments are used to form a reflector, but differing segments can configured for combination as a reflector as well. The segment 1002 includes a plurality of apertures such as representative aperture 1006 arranged in, for example, along a circular arc about a symmetry axis 1001. The apertures can be configured to receive respective optical fibers, optical fiber bundles, or optical elements such as lenses so that optical pulses are directed to a specimen surface. A housing 1004 defines an aperture 1008 configured to retain an acoustic transducer or a transducer array. Two segments such as the segment 1002 are secured to each other, and suitable optical fibers and acoustic transducers secured to the combined segments to form a PA probe.

Figure 11:
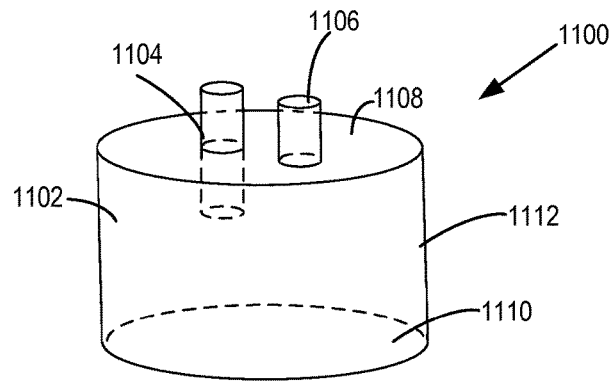
FIG. 11 is a perspective view of a PA probe that includes a plano-plano lens.

With reference to FIG. 11, a PA probe 1100 includes a plano-plano lens 1102 configured to retain an optical fiber 1104 for optical beam input and an acoustic transducer 1106 to receive acoustic signals at a surface 1108. A face surface 1110 is typically situated at a specimen surface, and acoustically coupled to the specimen surface with an acoustic gel. At least one of the face surface 1110 or a side surface 1112 is provided with a coating that reflects portions of optical pulses returned from a specimen so that these portions can be redirected to the specimen. The side surface 1112 can be sufficiently reflective based on total internal reflection, and only the surface 1108 provided with a coating. In some examples, only a portion of the surface 1108 is provided with a reflective coating.

With reference to FIG. 12, a representative PA imaging method 1200 includes applying one or more optical probe pulses to one or more target locations at 1202. At 1204, scattered or reflected portions of the optical probe pulses are collected and at 1206, these collected portions are redirected to the target locations. Photoacoustic signals responsive to the combined probe pulses and the collected scattered portions are detected at 1208. Specimen images or other specimen characterizations are produced at 1210.

In view of the many possible embodiments to which the principles of the disclosed technology may be applied, it should be recognized that the illustrated embodiments are only preferred examples and should not be taken as limiting the scope of the technology. In some examples, a probe reflective surface is situated so that a specimen surface is imaged by the reflective surface back onto the reflective surface, i.e., the reflective surface/specimen surface separation is twice a reflective surface focal length. Alternatively, the reflective surface can be situated to collimate captured light from the specimen surface. In some examples, total internal reflection can be used to enhance scattered light capture. Pulsed light sources are typically used in PAI, but continuous sources can be used in some examples. In addition, PA images are acquired by some systems, but other PA based specimen evaluations can be obtained with the disclosed probes. Accordingly, the disclosure should not be taken as limited to any particular embodiments, and we claim as our invention all that comes within the scope and spirit of the appended claims.

We claim:

1. A photoacoustic probe for delivering optical pulses to a target and receiving associated acoustic signals, the probe comprising:
    a light collector situated along an axis, the light collector defining a reflective surface on an inner or an outer surface of a concave shell situated to direct portions of an optical beam received from the target so as to return to the target, the reflective surface including:
        an optical input aperture defined in the reflective surface so as to couple the optical pulses to the target through a volume defined by the reflective surface and a reflective surface output aperture, and
        an acoustic aperture defined in the reflective surface and situated to receive acoustic signals produced at the target in response to the optical pulses and transmitted by the reflective surface output aperture to the volume defined by the reflective surface and the reflective surface output aperture; and
    an acoustic transducer situated at the acoustic aperture, wherein the acoustic transducer is secured to the concave shell, and an optical fiber is secured to the concave shell and configured to deliver the optical pulses to the target through the reflective surface output aperture.

2. The photoacoustic probe of claim 1, wherein the optical input aperture intersects and is orthogonal to the axis of the light collector.

3. The photoacoustic probe of claim 1, wherein the acoustic aperture intersects and is orthogonal to the axis of the light collector.

4. The photoacoustic probe of claim 1, wherein the reflective surface is situated at the inner surface of the concave shell.

5. The photoacoustic probe of claim 1, wherein the reflective surface is situated at the outer surface of the concave shell.

6. The photoacoustic probe of claim 1, wherein the acoustic transducer is secured to an exterior of the concave shell.

7. The photoacoustic probe of claim 1, wherein the optical input aperture and the acoustic aperture are defined by corresponding holes in the reflective surface.

8. The photoacoustic probe of claim 1, wherein the optical input aperture is defined by a light transmissive window in the reflective surface.

9. The photoacoustic probe of claim 1, wherein the acoustic transducer is fixed with respect to the reflective surface and the optical fiber is fixed with respect to the reflective surface.

10. The photoacoustic probe of claim 1, wherein the light collector comprises a transmissive face layer situated at the reflective surface output aperture, and configured to retain an acoustic index matching material so as to acoustically couple the acoustic aperture and the transmissive face layer.

11. The photoacoustic probe of claim 1, wherein the reflective surface is configured to reflect an infrared optical beam and transmit visible optical radiation.

12. The photoacoustic probe of claim 1, wherein the acoustic transducer is an acoustic transducer array.

13. A method, comprising:
    with the photoacoustic probe of claim 1,
    directing the optical pulses to the target;
    capturing at least a portion of the optical beam received from the target with the reflective surface; and
    directing the captured portion of the optical beam to the target from the reflective surface.

14. The method of claim 13, wherein the optical pulses are selected to provide a phototherapeutic exposure.

15. The method of claim 13, further comprising detecting the acoustic signals produced at the target responsive to the optical pulses and the captured portion of the optical beam.

16. The method of claim 13, wherein the at least a portion of the optical beam received from the target is captured with the inner surface of the concave shell.

17. The method of claim 13, wherein the at least a portion of the optical beam received from the target is captured with the outer surface of the concave shell.

18. The method of claim 13, wherein the captured portion of the optical beam received from the target is associated with reflection from a surface of the target.

19. The method of claim 13, wherein the surface of the target is skin.

20. The method of claim 13, further comprising processing a plurality of acoustic signals returned from the target so as to form a target image.

21. The method of claim 20, wherein the target is tissue, and further comprising applying a phototherapeutic optical beam to a selected location identified in the target image and the optical pulses and the phototherapeutic optical beam are coupled to the target through a beam diffusing reflective surface.

22. A photoacoustic imaging system, comprising:
a photoacoustic probe as recited in claim 1;
an optical pulse source coupled to the optical input aperture of the photoacoustic probe so as to direct the optical pulses to the target;
wherein the acoustic transducer is configured to detect the acoustic signals produced at the target in response to the optical pulses directed to the target; and
a signal processor configured to receive the detected acoustic signals and produce an image based on the detected acoustic signals.

23. The photoacoustic imaging system of claim 22, wherein the optical pulses are at a wavelength of between 700 nm and 3000 nm and the reflective surface is configured to transmit visible optical radiation such that the target is viewable through the concave shell.

24. The photoacoustic imaging system of claim 22, wherein the optical pulses are at near-infrared or infrared wavelengths and the reflective surface is configured to transmit visible optical radiation such that the target is viewable through the concave shell.

25. The photoacoustic probe of claim 1, wherein the concave shell is a spherical cap.

* * * * *